United States Patent [19]

Markezich et al.

[11] 4,276,233

[45] Jun. 30, 1981

[54] HINDERED PHENOL PHOSPHITES

[75] Inventors: Ronald L. Markezich; Walter K. Olander, both of Mt. Vernon, Ind.; Robert J. Axelrod, Glenmont, N.Y.

[73] Assignee: General Electric Company, Mt. Vernon, Ind.

[21] Appl. No.: 57,999

[22] Filed: Jul. 16, 1979

Related U.S. Application Data

[62] Division of Ser. No. 957,430, Nov. 2, 1978.

[51] Int. Cl.$^3$ .......................... C07F 9/141; C08K 5/52
[52] U.S. Cl. .................................. 260/937; 260/967; 260/45.95 D
[58] Field of Search ................................ 260/937, 967

[56] References Cited

U.S. PATENT DOCUMENTS

| | | | |
|---|---|---|---|
| 3,201,435 | 8/1965 | Schulz | 260/967 |
| 3,305,520 | 2/1967 | Fritz et al. | 260/45.7 PH |
| 3,467,733 | 9/1969 | Dever et al. | 260/937 |

FOREIGN PATENT DOCUMENTS 43-22092  9/1968  Japan ....................................... 260/967

*Primary Examiner*—Anton H. Sutto
*Attorney, Agent, or Firm*—Martin B. Barancik; William F. Mufatti

[57] ABSTRACT

Thermally stable polycarbonate compositions are obtained by admixing with a high molecular weight aromatic polycarbonate resin a stabilizing amount of a hindered phenol phosphite.

14 Claims, No Drawings

HINDERED PHENOL PHOSPHITES

This is a division of application Ser. No. 957,430, filed Nov. 2, 1978.

This invention relates to thermally stable polycarbonate compositions comprising an admixture of an aromatic polycarbonate and a stabilizing amount of a hindered phenol phosphite.

BACKGROUND OF THE INVENTION

In the past, much effort has been expended in preparing thermally stable polycarbonate compositions which would be color stable at elevated temperatures and particularly at the high molding temperatures generally employed to prepare molded polycarbonate articles. Many different additives have been found that are quite suitable for rendering polycarbonates heat and color stable. Particularly useful are triorgano phosphites such as are disclosed in U.S. Pat. No. 3,305,520. In addition, U.S. Pat. Nos. 3,729,440 and 3,953,338 disclose thermally stable aromatic polycarbonates containing a phosphinite and an epoxy compound. Further, U.S. Pat. No. 3,794,629 discloses chemically stable aromatic polycarbonates containing oxetane phosphites and U.S. Pat. No. 3,978,020 discloses thermally stable aromatic polycarbonates containing phosphonites which include epoxy compounds.

Polycarbonates are also used for producing bottles; however, these bottles become hazy after sterilization in water or exposure to moisture at elevated temperatures. U.S. Pat. No. 3,839,247 discloses a water clear polycarbonate composition which can be used to mold bottles wherein the polycarbonate composition contains an aromatic epoxy or an aliphatic epoxy compound as a stabilizer.

Copending application Ser. No. 957,426, filed Nov. 2, 1978, discloses aromatic polycarbonate compositions containing phosphonite oxetanes; copending application Ser. No. 957,429, filed Nov. 2, 1978, discloses aromatic polycarbonate compositions containing phosphite oxetanes having a hindered phenol; copending application Ser. No. 957,428, filed Nov. 2, 1978, discloses aromatic polycarbonate compositions containing a phosphonite or a phosphonite oxetane each having a hindered phenol; and, copending application Ser. No. 957,427, filed Nov. 2, 1978, discloses aromatic polycarbonate compositions containing dioxane phosphites, each of these copending applications being assigned to the same assignee as this case.

DESCRIPTION OF THE INVENTION

It has been discovered that when an aromatic polycarbonate is admixed with a hindered phenol phosphite, the resulting polycarbonate composition has improved thermal stability as exemplified by its resistance to yellowing when subjected to high molding temperatures.

The phosphite compounds that can be used in the present invention are represented by the general structure:

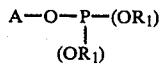

wherein $R_1$ can be an alkyl of $C_1$ to $C_{30}$, an aryl of $C_6$ up to about $C_{30}$, preferably $C_6-C_{12}$, and alkyls of $C_2$ to $C_{20}$ which can form cyclic structures; and, A is a hindered phenol represented by the general structure:

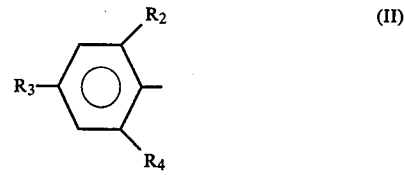

wherein $R_2$, $R_3$ and $R_4$ can be the same or different and each can independently be hydrogen, halogen or $C_1-C_4$ alkyl provided that neither $R_2$ and/or $R_4$ are hydrogen.

Thus, $R_1$ in formula I can be unsubstituted and halogen substituted alkyl, aryl, cycloalkyl, aralkyl and alkaryl radicals of about $C_1-C_{30}$ so that typical phosphites that can be employed in the present invention are those wherein $R_1$ can be alkyl such as methyl, ethyl, n-propyl, isopropyl, n-butyl, sec-butyl, tertiary butyl, n-amyl, isoamyl, tertiary amyl, n-hexyl, dodecyl, nonyl, and the like; cycloalkyl such as cyclohexyl, 2-methylcyclohexyl, 4-methylcyclohexyl, 2-ethylcyclohexyl, 4-ethylcyclohexyl, 4-isopropylcyclohexyl, and the like; aryl such as phenyl, naphthyl, 2-naphthyl, biphenyl of terphenyl, and the like; aralkyl such as benzyl, phenylethyl, 2-phenylethyl, 1-phenylpropyl, 2-phenylpropyl, and the like; alkaryl such as p-tolyl, m-tolyl, 2,6-xylyl, o-tolyl, p-cumyl, m-cumyl, o-cymyl, mesityl, p-tertiary butylphenyl, and the like; and, haloaryl such as 2-chlorophenyl, 2,4,6-trichlorophenyl, 2,4,6-tribromophenyl, and the like, wherein the substituted portions thereof can be halogen atoms.

The phosphites of the invention can be prepared by methods known to those skilled in the art such as are described in *Organic Phosphorus Compounds*, Vol. 4, edited by G. M. Kosolapoff and L. Maier (1972), pages 255–462, which is incorporated herein by reference thereto.

The phosphite compounds of the invention are admixed with the aromatic polycarbonate in a stabilizing amount which is generally on the order of about 0.005–1.0, preferably 0.01–0.50 and optimumly and 0.02–0.20 weight percent, based upon the weight of the aromatic polycarbonate.

The aromatic polycarbonate that can be employed in the practice of this invention are homopolymers and copolymers, and mixtures thereof that are prepared by reacting a dihydric phenol with a carbonate precursor.

The dihydric phenols that can be employed are bisphenols such as bis(4-hydroxyphenyl)methane, 2,2-bis(4-hydroxyphenyl)propane (bisphenol-A), 2,2-bis(4-hydroxy-3-methylphenyl)propane. 4,4-bis(4-hydroxyphenyl)heptane, 2,2-bis(4-hydroxy-3,5-dichlorophenyl)-propane, 2,2-bis(4-hydroxy-3,5-dibromophenyl)propane, etc.; dihydric phenol ethers such as bis(4-hydroxyphenyl)ether, bis(3,5-dichloro-4-hydroxyphenyl)ether, etc.; dihydroxydiphenyls such as p,p'-dihydroxydiphenyl, 3,3'-dichloro-4,4-dihydroxydiphenyl, etc.; dihydroxyaryl sulfones such as bis(4-hydroxyphenyl)sulfone, bis(3,5-dimethyl-4-hydroxyphenyl)sulfone, etc.; dihydroxy benzenes, resorcinol, hydroquinone, halo- and alkyl-substituted dihydroxybenzenes such as 1,4-dihydroxy-2,5-dichlorobenzene, 1,4-dihydroxy-3-methylbenzene, etc.; and dihydroxy diphenyl sulfoxides such as bis(4-hydroxyphenyl)sulfoxide, bis(3,5-dibromo-4-hydroxyphenyl)sulfoxide, etc. A variety of additional dihydric phenols are also available to provide carbonate polymers such as are disclosed in U.S. Pat. Nos. 2,999,835, 3,028,365 and 3,153,008. Also suited for preparing the aromatic carbonate polymers are copolymers prepared from the above dihydric phenols copolymerized with halogen-containing dihydric phenols such as 2,2-bis(3,5-dichloro-4-hydroxyphenyl)propane, 2,2-bis(3,5-dibromo-4-hydroxyphenyl)propane, etc. It is also possible to employ two or more different dihydric phenols or a copolymer of a dihydric phenol with a glycol or with hydroxy or acid terminated polyester, or with a dibasic acid in the event a carbonate copolymer or interpolymer rather than a homopolymer is desired for use in the preparation of the aromatic polycarbonates of this invention as well as blends of any of the above materials.

The carbonate precursor can be either a carbonyl halide, a carbonate ester or a haloformate. The carbonyl halides which can be employed are carbonyl bromide, carbonyl chloride and mixtures thereof. Typical of the carbonate esters that can be employed are diphenyl carbonate, di-(halophenyl)carbonates such as di-(chlorophenyl)carbonate, di-(bromophenyl)carbonate, di-(trichlorophenyl)carbonate, di-(tribromophenyl)carbonate, etc., di-(alkylphenyl)carbonate such as di-(tolyl)carbonate, etc., di-(naphthyl)carbonate, di-(chloronaphthyl)carbonate, phenyl tolyl carbonate, chlorophenyl chloronaphthyl carbonate, etc., or mixtures thereof. The haloformates suitable for use herein include bishaloformates of dihydric phenols (bischloroformates of hydroquinone, etc.) or glycols (bishaloformates of ethylene glycol, neopentyl glycol, polyethylene glycol, etc.). While other carbonate precursors will occur to those skilled in the art, carbonyl chloride, also known as phosgene, is preferred.

Also included are the polymeric derivatives of a dihydric phenol, a dicarboxylic acid and carbonic acid. These are disclosed in U.S. Pat. No. 3,169,121 which is incorporated herein by reference.

The aromatic polycarbonates of this invention are prepared by employing a molecular weight regulator, an acid acceptor and a catalyst. The molecular weight regulators which can be employed include monohydric phenols such as phenol, chroman-I, paratertiarybutylphenol, parabromophenol, primary and secondary amines, etc. Preferably, phenol is employed as the molecular weight regulator.

A suitable acid acceptor can be either an organic or an inorganic acid acceptor. A suitable organic acid acceptor is a tertiary amine and includes such materials as pyridine, triethylamine, dimethylaniline, tributylamine, etc. The inorganic acid acceptor can be one which can be either a hydroxide, a carbonate, a bicarbonate, or a phosphate of an alkali or alkaline earth metal.

The catalysts which can be employed can be any of the suitable catalyst that aid the polymerization of bisphenol-A with phosgene. Suitable catalysts include tertiary amines such as triethylamine, tripropylamine, N,N-dimethylaniline, quaternary ammonium compounds such as tetraethylammonium bromide, cetyl triethylammonium bromide, tetra-n-heptylammonium iodide, tetra-n-propylammonium bromide, tetramethylammonium chloride, tetramethylammonium hydroxide, tetra-n-butylammonium iodide, benzyltrimethylammonium chloride and quaternary phosphonium compounds such as n-butyl-triphenyl phosphonium bromide and methyltriphenyl phosphonium bromide.

Also included herein are branched polycarbonates wherein a polyfunctional aromatic compound is reacted with the dihydric phenol and carbonate precursor to provide a thermoplastic randomly branched polycarbonate.

These polyfunctional aromatic compounds contain at least three functional groups which are carboxyl, carboxylic anhydride, haloformyl or mixtures thereof. Examples of these polyfunctional aromatic compounds include trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride, and the like. The preferred polyfunctional aromatic compounds are trimellitic anhydride or trimellitic acid, or their haloformyl derivatives.

Also included herein are blends of a linear polycarbonate and a branched polycarbonate.

DESCRIPTION OF THE PREFERRED EMBODIMENT

The following examples are set forth to more clearly illustrate the invention. Unless otherwise specified, parts or percents are by weight.

EXAMPLE 1

Method of Preparing A New Phosphite

Diphenyl-(2,4,6-trimethylphenyl)phosphite 276 grams (2.94 moles) of phenol and 200 grams (1.47 moles) of 2,4,6-trimethylphenol were heated at 50° C. under nitrogen until melted and then 201.9 grams (1.47 moles) of phosphorous trichloride were added dropwise. When the phosphorous trichloride addition was complete, the mixture was heated to 100° C. and held at this temperature overnight. Vacuum was applied and unreacted phenol and trimethylphenol were distilled off. The product, diphenyl-(2,4,6-trimethylphenyl)-phosphite, was distilled at 165° to 170° C. at 0.1 mm.Hg. to afford a clear colorless liquid. The proton nuclear magnetic resonance (NMR) analysis showed the methyl protons at 2.27 δ (9.1 H) and the aromatic protons at 6.80 and 7.15 δ (11.9 H).

Structure:

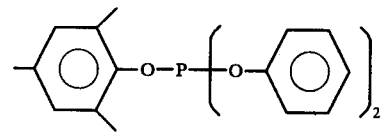

EXAMPLE 2

Method of Preparing A New Phosphite

Bis(2,4,6-trimethylphenyl)phenyl phosphite 103.6 grams (1.1 moles) of phenol and 300 grams (2.2 moles) of 2,4,6-trimethylphenol were heated at 50° C. under nitrogen until melted and then 151.1 grams (1.1 moles) of phosphorous trichloride were added dropwise. When the phosphorous trichloride addition was complete, the mixture was heated at 100° C. and held at this temperature overnight. Vacuum was applied and unreacted phenol and trimethylphenol distilled off. The product, bis(2,4,6-trimethylphenyl)phenyl phosphite, was distilled at 187° to 190° C. at 0.35 mm.Hg. to afford a clear colorless liquid. The proton NMR showed the methyl protons at 2.27 δ (17.2 H) and the aromatic protons at 6.80 and 7.15 δ (9.8 H).

Structure:

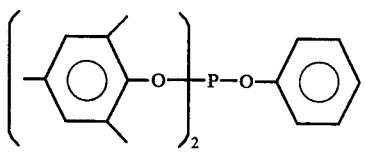

EXAMPLE 3

Method of Preparing A New Phosphite

Tris(2,4,6-trimethylphenyl)phosphite 300 grams (2.2 moles) of 2,4,6-trimethylphenol were heated under nitrogen until melted and then 89.9 grams (0.65 mole) of phosphorous trichloride were added dropwise. When the addition was complete, the mixture was heated to 100° C. and held at this temperature overnight. Vacuum was applied and unreacted trimethylphenol distilled off. The product, tris(2,4,6-trimethylphenyl)phosphite, was distilled at 172°–174° C. at 0.3 mm.Hg. to afford a clear colorless liquid which solidified on standing, mp 92°–95° C. The proton NMR showed the methyl protons at 2.23 δ (27 H) and the aromatic protons at 6.77 δ (6 H).

Structure:

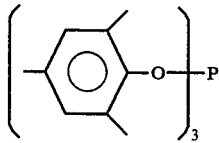

EXAMPLE 4

Method of Preparing a New Phosphite

Diphenyl-(2,4-di-t-butylphenyl)phosphite 564.7 grams (6 moles) of phenol and 619 grams (3 moles) of 2,4-di-t-butylphenol were heated at 50° C. under nitrogen until melted and then 412.1 grams (3 moles) of phosphorous trichloride were added dropwise. When the addition was complete, the mixture was heated to 100° C. and held at this temperature overnight. Vacuum was applied and unreacted phenol and di-t-butylphenol distilled off. The product, diphenyl-(2,4-di-t-butylphenyl)phosphite, was distilled at 175° to 180° C. at 0.15 mm.Hg. to afford a pale yellow liquid. The proton NMR showed the t-butyl protons at 1.3 δ (19.8 H) and the aromatic protons at 7.1 δ (10.2 H).

Structure:

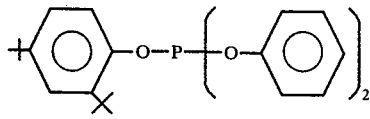

EXAMPLE 5

Method of Preparing a New Phosphite

Bis(2,4-di-butylphenyl)phenyl phosphite 70.5 grams (0.75 mole) of phenol and 309.5 grams (1.5 moles) of 2,4-di-t-butylphenol were heated at 50° C. under nitrogen until melted and then 96.2 grams (0.7 mole) of phosphorous trichloride were added dropwise. When the addition was complete, the mixture was heated to 100° C. and held at this temperature overnight. Vacuum was applied and unreacted phenol and di-t-butylphenol distilled off. The product, bis(2,4-di-t-butylphenyl)phenyl phosphite, was distilled at 180° C. at 0.2 mm.Hg. to afford a pale yellow liquid. The proton NMR showed the t-butyl protons at 1.3 δ (33.4 H) and the aromatic protons at 7.2 δ (13.6 H).

Structure:

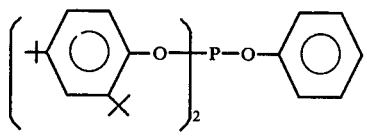

EXAMPLE 6

Method of Preparing A New Phosphite

Diphenyl-(2,6-dimethylphenyl)phosphite 769.8 grams (8.18 moles) of phenol and 500 grams (4.09 moles) of 2,6-dimethylphenol were heated at 50° C. under nitrogen until melted and then 561.7 grams (4.09 moles) of phosphorous trichloride were added dropwise. When the addition was complete, the mixture was heated to 100° C. and held at this temperature overnight. Vacuum was applied and unreacted phenol and dimethylphenol distilled off. The product, diphenyl-(2,6-dimethylphenyl)phosphite, was distilled at 155° C. at 0.2 mm.Hg. to afford a clear colorless liquid. The proton NMR showed the methyl protons at 2.33 δ (5.16 H) and the aromatic protons at 7.00 and 7.17 δ (13.4 H).

Structure:

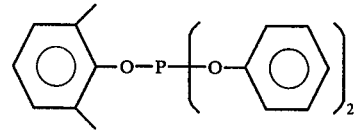

EXAMPLE 7

Method of Preparing A New Phosphite

Bis(2,6-dimethylphenyl)phenyl phosphite 280 grams (2.04 moles) of phenol and 500 grams (4.09 moles) of 2,6-dimethylphenol were heated at 50° C. under nitrogen until melted and then 192 grams (2.04 moles) of phosphorous trichloride were added dropwise. When the addition was complete, the mixture was heated to 100° C. and held at this temperature overnight. Vacuum was applied and unreacted phenol and dimethylphenol distilled off. The product, bis(2,6-dimethylphenyl)phenyl phosphite, was distilled at 155° to 165° C. at 0.2 mm.Hg. to afford a clear colorless liquid. The proton NMR showed the methyl protons at 2.33 δ

(11.4 H) and the aromatic protons at 7.00 and 7.17 δ (11.6 H).

Structure:

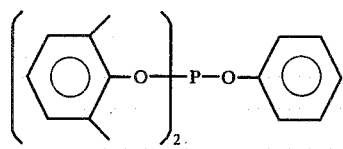

EXAMPLE 8

Method of Preparing A New Phosphite

Di-n-octyl-(2,4,6-trimethylphenyl)phosphite 50 grams (0.14 mole) of diphenyl-(2,4,6-trimethylphenyl)phosphite, 40 grams (0.31 mole) of 1-octanol, and 0.25 grams of sodium methoxide were heated under a vacuum of 30 mm.Hg. Phenol was removed from the reaction mixture through a Vigreaux column at a pot temperature of 130° C. and a head temperature of 93° C. at 30 mm.Hg. The pot temperature was increased to 160° C. and the pressure reduced to 0.2 mm.Hg. to insure complete removal of phenol and excess octanol. The product, di-n-octyl-(2,4,6-trimethylphenyl)phosphite, was distilled at 138° to 139° C. at 0.2 mm.Hg. to afford a clear colorless liquid. The proton NMR showed aliphatic protons centered at 0.85 and 1.3 δ, the methyl groups of the trimethylphenyl moiety at 2.3 δ, the methylene groups adjacent to the oxygen at 3.95 δ, and the aromatic protons at 7.0 δ

Structure:

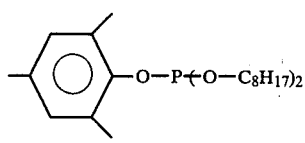

EXAMPLE 9

Method of Preparing A New Phosphite

Di(2-ethyl-1-hexyl)-(2,4,6-trimethylphenyl)phosphite 50 grams (0.14 mole) of diphenyl-(2,4,6-trimethylphenyl)phosphite, 40 grams (0.31 mole) of 2-ethyl-1-hexanol, and 0.25 grams of sodium methoxide were heated under a vacuum of 30 mm.Hg. Phenol was removed from the reaction mixture through a Vigreaux column at a head temperature of 94° C. at 30 mm.Hg. The pot temperature was increased to 160° C. and the pressure reduced to 0.2 mm.Hg. to insure complete removal of phenol and excess hexanol. The product, di(2-ethyl-1-hexyl)-)2,4,6-trimethylphenyl)phosphite, was distilled at 150° to 155° C. at 0.2 mm.Hg. to afford a clear colorless liquid. The proton NMR showed aliphatic protons centere at 0.9 and 1.3 δ, the methyl groups of the trimethylphenyl moiety at 2.55 δ, the methylene group adjacent to the oxygen at 3.95 δ, and the aromatic protons at 7.0 δ.

Structure:

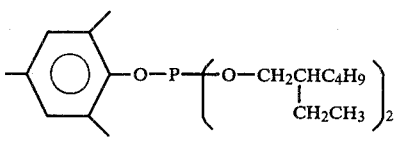

EXAMPLE 10

Method of Preparing A New Phosphite

Di-2-octyl-(2,4,6-trimethylphenyl)phosphite 50 grams (0.14 mole) of diphenyl-(2,4,6-trimethylphenyl)phosphite, 40 grams (0.31 mole) of 2-octanol, and 0.25 grams of sodium methoxide were heated under a vacuum of 30 mm.Hg. at 100° C. Phenol was removed from the reaction mixture through a Vigreaux column at a head temperature of 94° C. at 30 mm.Hg. The pot temperature was increased to 160° C. and the pressure reduced to 0.2 mm.Hg. to insure complete removal of phenol and excess octanol. The product, di-2-octyl-(2,4,6-trimethylphenyl)phosphite, was distilled at 168° C. at 0.2 mm.Hg. to afford a clear colorless liquid. The proton NMR showed aliphatic protons centered at 0.85 and 1.3 δ, the methyl groups of the trimethylphenyl moiety at 2.25 δ, the methine groups adjacent to the oxygen at 4.4 δ, and the aromatic protons at 6.8 δ.

Structure:

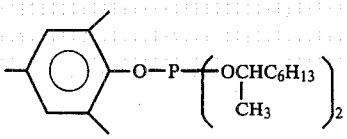

EXAMPLE 11

Method of Preparing a New Phosphite 2,4,6-Trimethylphenyl neopentyl phosphite 144.8 grams (0.41 mole) of diphenyl-(2,4,6-trimethylphenyl)phosphite, 42.7 grams (0.41 mole) of dimethyl propanediol and 0.5 grams of sodium methoxide were heated under a vacuum of 30 mm.Hg. Phenol was removed from the reaction mixture through a Vigreaux column at a head temperature of 94° C. at 30 mm.Hg. The pot temperature was increased to 160° C. for 3 hours to insure complete removal of phenol. The product, 2,4,6-trimethylphenyl neopentyl phosphite was distilled at 127° to 130° C. at 0.35 mm.Hg. to afford a clear colorless liquid. The proton NMR showed aliphatic protons at 0.6 and 1.2 δ, the methyl groups of the trimethylphenyl moiety at 2.2 δ, the methylene groups adjacent to the oxygen at 3.4 and 4.3 δ, and the aromatic protons at 6.8 δ.

Structure:

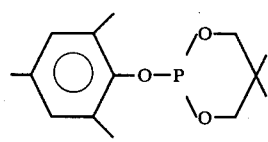

EXAMPLE 12

Method of Preparing a New Phosphite 2,4-Di-t-butylphenyl neopentyl phosphite 150 grams (0.36 mole) of diphenyl-(2,4,-di-t-butylphenyl)phosphite, 37 grams (0.36 mole) of dimethyl propanediol, and 0.5 grams of sodium methoxide were heated under a vacuum of 30 mm.Hg. Phenol was removed from the reaction mixture through a Vigreaux column at a head temperature of 94° C. at 30 mm.Hg. The pot temperature was increased to 160° C. for 3 hours to insure complete removal of phenol. The product, 2,4-di-t-butylphenyl neopentyl phosphite was distilled at 110° C. at 0.1 mm.Hg. to afford a clear colorless liquid which solidified to a white solid upon standing (m.p. 68°-73° C.). The proton NMR showed aliphatic protons from 0.6 to 1.5 δ, the methylene groups adjacent the oxygen at 3.5 and 4.3 δ, and the aromatic protons centered at 7.2 δ.

Structure:

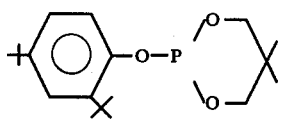

EXAMPLE 13

Method of Preparing a New Phosphite 2,6-Dimethylphenyl neopentyl phosphite 270 grams (0.8 mole) of diphenyl-(2,6-dimethylphenyl)phosphite, 104.2 grams (1.0 mole) of dimethyl propanediol, and 0.5 grams of sodium methoxide were heated under a vacuum of 30 mm.Hg. Phenol was removed from the reaction mixture through a Vigreaux column at a head temperature of 94° C. at 30 mm.Hg. The pot temperature was increased to 160° C. for 3 hours to insure complete removal of phenol. The product, 2,6-dimethylphenyl neopentyl phosphite, was distilled at 95° C. to 115° C. at 0.4 mm.Hg. to afford a clear colorless liquid. The proton NMR showed aliphatic protons from 0.8 to 1.4 δ, the methyl groups of the dimethylphenyl moiety at 2.3 δ, the methylene groups adjacent the oxygen at 3.4 and 4.3 δ, and the aromatic protons at 7.2 δ.

Structure:

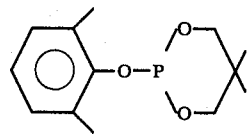

EXAMPLE 14

A polycarbonate composition of a homopolymer of 2,2-bis(4-hydroxyphenyl)propane (bisphenol-A) was prepared by reacting essentially equimolar amounts of bisphenol-A and phosgene in an organic medium with triethylamine, sodium hydroxide and phenol under standard conditions and was mixed with the stabilizers shown in Table I plus a trace amount of a commercially obtained blue pigment by tumbling the ingredients in a laboratory tumbler. This mixture was then fed to an extruder, which extruder was operated at about 500° F., and the extruded strands chopped into pellets. The pellets were then injected molded at 600° F. and 680° F. into test samples of about 3 inches by 2 inches by ⅛ inch thick. Thermal stability to discoloration of the test sample was measured in accordance with ASTM Yellowness Index (YI) Test D1925 on samples molded at 600° F. and 680° F. The results obtained are set forth in TABLE I below.

TABLE I

| | | Thermal Stability | |
|---|---|---|---|
| | Amount | YI of Test Samples Molded At: | |
| Stabilizer | (wt %) | 600° F. | 680° F. |
| *A | 0.1 | 3.1 | 10.1 |
| Example 1 | 0.04 | 2.6 | 5.5 |
| Example 1 | 0.08 | 2.6 | 5.7 |
| Example 2 | 0.04 | 2.8 | 6.1 |
| Example 2 | 0.08 | 2.4 | 5.9 |
| Example 3 | 0.05 | 2.9 | 5.7 |
| Example 3 | 0.10 | 2.8 | 6.0 |

*As disclosed in Ger. Pat. 1,694,285 and referred to in U.S. Pat. No. 3,794,629: 1 part octyldiphenyl phosphite ⁊ parts 3,4-epoxy-cyclohexylmethyl-3,4-epoxycyclohexane carboxylate The test samples molded at 680° F. were subjected to accelerated heat aging by placing them in an oven at 140° C. for a period of 1 week and 2 weeks. The results obtained are shown in TABLE II below.

TABLE II

| | | YI of Heat Aged 680° F. Molded Test Samples After | | |
|---|---|---|---|---|
| | Amount | | | |
| Stabilizer | (wt %) | Initial | 1 week | 2 weeks |
| A | 0.1 | 10.1 | 20.7 | 28.2 |
| Example 1 | 0.04 | 5.5 | 14.3 | 22.3 |
| Example 1 | 0.08 | 5.7 | 14.0 | 23.8 |
| Example 2 | 0.04 | 6.1 | 15.6 | 23.2 |
| Example 2 | 0.08 | 5.9 | 14.6 | 23.6 |
| Example 3 | 0.05 | 5.7 | 15.8 | 23.9 |
| Example 3 | 0.1 | 6.0 | 14.7 | 24.4 |

The results in TABLES I and II above reveal that all of the Example 1, 2 and 3 stabilizers of the invention imparted significantly better thermal stability than did prior art stabilizer A, even when employed at noticeably lower concentrations.

EXAMPLE 15

A polycarbonate composition was prepared as described in Example 14 and admixed with stabilizers, extruded, and molded into test samples and the YI of the test samples was determined as described in Example 14. The results are shown in Table III below.

TABLE III

| | THERMAL STABILITY | | |
|---|---|---|---|
| | Amount | YI of Test Samples Molded at | |
| Stabilizer | (Wt. %) | 600° F. | 680° F. |
| A | 0.1 | 2.0 | 6.4 |
| Example 4 | 0.04 | 2.1 | 3.7 |
| Example 4 | 0.08 | 1.6 | 4.7 |

From the results shown in Table III above, it can be seen that the Example 4 stabilizer of the invention, even when employed at lower concentrations, imparted comparable or improved thermal stability over prior art stabilizer A, particularly at the higher 680° F. molding temperature.

EXAMPLE 16

A polycarbonate composition was prepared as described in Example 14 and admixed with stabilizers, extruded, and molded into test samples. The YI of the test samples was determined as described in Example 14 and are shown in Table IV below wherein "Control" identifies a polycarbonate composition without stabilizer.

TABLE IV

| | THERMAL STABILITY | | |
|---|---|---|---|
| | Amount | YI of Test Samples Molded at | |
| Stabilizer | (Wt. %) | 600° F. | 680° F. |
| Control | — | 3.3 | 8.1 |
| A | 0.1 | 2.0 | 5.7 |
| Example 8 | 0.04 | 2.0 | 4.9 |
| " | 0.08 | 1.8 | 4.4 |
| Example 9 | 0.04 | 1.9 | 4.7 |
| " | 0.08 | 1.8 | 4.8 |
| Example 10 | 0.04 | 2.3 | 4.4 |
| " | 0.08 | 2.0 | 4.1 |

From the results shown in Table IV above, it can be seen that the stabilizers of Examples 8, 9 and 10, although used at lower concentrations, imparted thermal stability comparable to that of prior art stabilizer A at the 600° F. molding temperature. However, thermal stability of the invention stabilizers show a marked improvement over stabilizer A at the elevated molding temperature of 680° F.

EXAMPLE 17

A polycarbonate composition was prepared as described in Example 14 and admixed with stabilizers, extruded and molded into test samples. The YI of the test samples was determined as described in Example 14 and the results obtained are shown in Table V below wherein "Control" identifies the polycarbonate composition without stabilizer.

TABLE V

| | Thermal Stability | | |
|---|---|---|---|
| | Amount | YI of Test Samples Molded At | |
| Stabilizer | (Wt. %) | 600° F. | 680° F. |
| Control | — | 3.5 | 6.3 |
| A | 0.1 | 2.1 | 6.9 |
| *B | 0.025 | 2.2 | 4.0 |
| *B | 0.05 | 1.8 | 4.1 |
| Example 11 | 0.03 | 1.9 | 3.7 |
| Example 11 | 0.06 | 1.7 | 2.9 |
| Example 12 | 0.035 | 1.7 | 3.4 |
| Example 12 | 0.07 | 1.6 | 3.5 |

*As disclosed in U.S. Pat. No. 3,509,091: phenyl neopentyl phosphite.

As can be seen from the results in Table V, the stabilizers of Examples 11 and 12 exhibit significantly better thermal stability than prior art stabilizers A or B at about comparable concentrations, particularly at the higher molding temperature of 680° F.

EXAMPLE 18

The molded test samples of Example 17 were also subjected to ASTM D-1003 to measure their light transmission before and after they were steam autoclaved at 250° F. to determine their hydrolytic stability. The results obtained are shown in TABLE VI below:

TABLE VI

| | Hydrolytic Stability | | |
|---|---|---|---|
| | % Light Transmission Stabilizer (Wt. %) | | |
| Time (hrs.) | B (0.025) | Example 11 (0.03) | Example 12 (0.035) |
| 0 | 87.6 | 87.7 | 87.6 |
| 24 | 47.7 | 80.8 | 87.1 |
| 48 | 3.2 | 15.3 | 84.1 |
| 72 | — | — | 63.2 |

The results in Table VI above reveal that the hydrolytic stability of polycarbonate compositions containing the stabilizers of Examples 11 and 12 are significantly superior to prior art stabilizer B which failed before the end of 24 hours, the failure level being generally acknowledged when the light transmission level falls below about 75%.

EXAMPLE 19

Following the procedure of Example 14, a polycarbonate composition was prepared, admixed with stabilizers, extruded and then molded into test samples. The YI of the test samples was determined as described in Example 14 and the results obtained are set forth in TABLE VII below:

TABLE VII

| | Thermal Stability | | |
|---|---|---|---|
| | | YI of Test Samples | |
| Stabilizer | (Wt. %) | 600° F. | 680° F. |
| A | 0.1 | 2.2 | 7.3 |
| Example 13 | 0.03 | 1.8 | 3.8 |
| Example 13 | 0.06 | 1.5 | 3.2 |

From the results in Table VII above, it can be seen that the stabilizer of the invention imparts significantly superior thermal stability to polycarbonate compositions than prior art stabilizer A, even at much less concentration levels.

Although the stabilizers of the invention have been particularly shown employed with high molecular weight aromatic polycarbonates, it should be understood that this has been by way of illustrating the general efficacy of these stabilizers with thermoplastic resins. As will be apparent to the skilled artisan, the stabilizers of the invention can also be employed with other thermoplastics such as polyolefins, polyvinyl chloride, polyesters and the like, with substantially similar facility and efficacy.

What is claimed is:

1. A phosphite compound represented by the general structure:

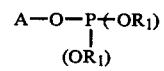

wherein $R_1$ can independently be an alkyl of about $C_1$-$C_{30}$; and alkyls of $C_2$-$C_{20}$ which can form cyclic structures; and, A is a hindered phenol represented by the general structure:

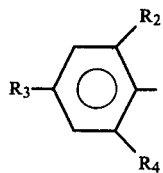

wherein $R_2$, $R_3$ and $R_4$ can be the same or different and each can independently be hydrogen, halogen or $C_1$-$C_4$ alkyl provided that neither $R_2$ and/or $R_4$ are both hydrogen.

2. A phosphite compound having the structure:

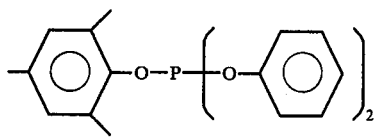

3. A phosphite compound having the structure:

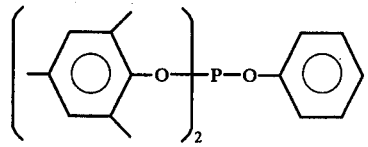

4. A phosphite compound having the structure:

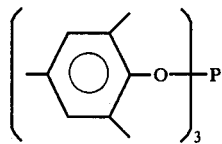

5. A phosphite compound having the structure:

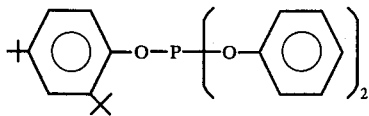

6. A phosphite compound having the structure:

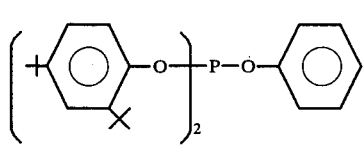

7. A phosphite compound having the structure:

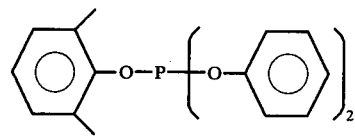

8. A phosphite compound having the structure:

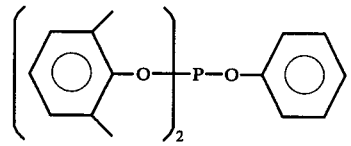

9. A phosphite compound having the structure:

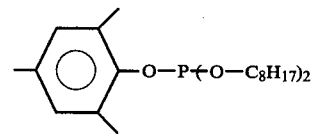

10. A phosphite compound having the structure:

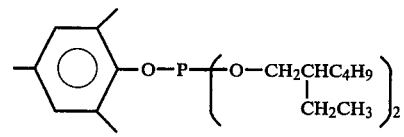

11. A phosphite compound having the structure:

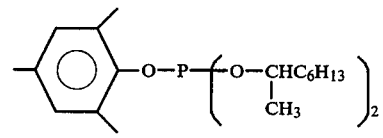

12. A phosphite compound having the structure:

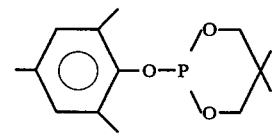

13. A phosphite compound having the structure:

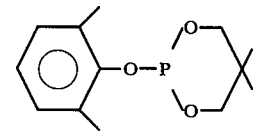

14. A phosphite compound having the structure:

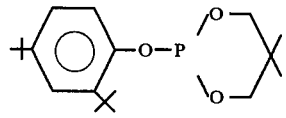

* * * * *